(12) United States Patent
Poo et al.

(10) Patent No.: US 7,790,437 B2
(45) Date of Patent: Sep. 7, 2010

(54) ORGAN TRANSPORTATION DEVICE

(75) Inventors: Ramon E. Poo, Miami, FL (US);
Camillo Ricordi, Miami, FL (US)

(73) Assignees: Biorep Technologies, Inc., Miami, FL (US); The University of Miami, Miami, FL (US)

( * ) Notice: Subject to any disclaimer, the term of this patent is extended or adjusted under 35 U.S.C. 154(b) by 901 days.

(21) Appl. No.: 11/610,913

(22) Filed: Dec. 14, 2006

(65) Prior Publication Data
US 2008/0145833 A1 Jun. 19, 2008

(51) Int. Cl.
*A01N 1/00* (2006.01)
*A01N 1/02* (2006.01)
*C12M 1/00* (2006.01)
*C12M 3/00* (2006.01)

(52) U.S. Cl. .............. 435/284.1; 435/1.1; 435/1.2; 435/298.2; 435/307.1; 435/298.1; 366/297; 366/298; 366/299; 366/300

(58) Field of Classification Search .......... 435/1.1, 435/1.2, 298.2, 284.1, 307.1, 298.1; 366/297, 366/298, 299, 300
See application file for complete search history.

(56) References Cited

U.S. PATENT DOCUMENTS

| 4,176,970 | A | * | 12/1979 | Blaetz .................. 366/280 |
| 4,246,864 | A | | 1/1981 | Pasternack et al. |
| 4,600,114 | A | | 7/1986 | Dabich |
| 4,714,595 | A | | 12/1987 | Anthony et al. |
| 5,066,578 | A | | 11/1991 | Wikman-Coffelt |
| 5,437,998 | A | * | 8/1995 | Schwarz et al. .......... 435/298.2 |
| 5,498,427 | A | | 3/1996 | Menasche |
| 5,752,929 | A | | 5/1998 | Klatz et al. |
| 5,928,945 | A | * | 7/1999 | Seliktar et al. ............. 435/395 |
| 5,960,708 | A | | 10/1999 | De Temple et al. |
| 6,019,237 | A | | 2/2000 | Durham et al. |
| 6,264,891 | B1 | | 7/2001 | Heyneker et al. |
| 6,490,880 | B1 | | 12/2002 | Walsh |
| 6,492,103 | B1 | | 12/2002 | Taylor |
| 6,566,126 | B2 | | 5/2003 | Cadwell |
| 6,593,136 | B1 | | 7/2003 | Geiss |
| 6,673,594 | B1 | | 1/2004 | Owen et al. |
| 2006/0223175 | A1 | * | 10/2006 | Hu et al. .................. 435/298.1 |
| 2007/0275363 | A1 | * | 11/2007 | Bertram et al. ............. 435/1.2 |
| 2008/0166796 | A1 | * | 7/2008 | Quinn et al. ............. 435/289.1 |

FOREIGN PATENT DOCUMENTS

| FR | 2 086 654 A | 12/1971 |
| GB | 1 305 905 A | 2/1973 |
| WO | WO 84/01082 A | 3/1984 |

* cited by examiner

*Primary Examiner*—Nathan A Bowers
(74) *Attorney, Agent, or Firm*—Novak Druce + Quigg LLP; Gregory A. Nelson

(57) ABSTRACT

An organ transportation device includes a fluid-tight organ container and structure within the organ container for engaging an organ within the organ container. A base assembly is provided, and structure for rotating the organ engaging structure and the organ relative to the base assembly. The base assembly can have a motor and a battery to provide for rotation of the organ container during shipping.

6 Claims, 10 Drawing Sheets

ORGAN TRANSPORTATION DEVICE

BACKGROUND OF THE INVENTION

The period between harvesting an organ and transplantation of the organ or cells from the organ into the recipient usually involves cold storage and transportation. During this period, the supply of blood, and consequently oxygen, is cut off from the organ. This period of cold ischemia is, at present, unavoidable and results in the gradual deterioration of cell function, eventually progressing to irreversible damage.

A new rapidly emerging technique for improved preservation of donor pancreata and possibly other organs has been established. The technique is called the 2 layer method and calls for the utilization of a solution of perfluorocarbon (PFC) or other oxygen-dissolving solution in combination with a cold storage preservation solution such as the University of Wisconsin preservation solution (the "UW solution"). The UW solution contains as its primary agents lactobionate and raffinose. These compounds are too large to enter the cells and therefore remain in the extracellular spaces. These impermeants act through osmotic forces to prevent cell swelling that would otherwise damage the stored organ.

Liver is another common organ for transplantation, as transplantation can be the only option for many patients suffering from some liver diseases. A successful transplantation requires that the donor liver be optimally preserved. Although the liver can be preserved for 10-20 hours, its cellular energy levels fall to critically low values within the first 1-4 hours. The consequences of a poorly functioning transplanted liver are potentially fatal, and requires re-transplantation at a significant increase in cost. It is therefore vital that adequate procedures and systems be provided for organ storage and transportation.

It is a well known fact that maintaining an organ partially submerged in oxygenated PFC greatly extends its useful life for transplantation or for cell procurement. The density of most organs is approximately 1 g/cm$^3$. The density of PFC is approximately 2 times that of the organ or 1.95 g/cm$^3$ and the density of the UW solution is approximately equal to that of the organ. Accordingly, the PFC settles at the bottom of the container while the UW solution settles on top of it. The organ typically rests partially submerged in the PFC while also being contacted by the UW solution. It is difficult to maintain this partial submersion especially during transportation of the organ because of the different sizes and shapes of organs and because the position of the container may also change.

Walsh, U.S. Pat. No. 6,490,880, discloses a regulated organ containment shipping system using dual-layer preservation liquid. The organ containment shipping system has an outer container adapted to receive a passive cooling medium and an inner container positioned within the outer container by structure that includes a gimbal mechanism to substantially maintain the inner container in a predefined orientation in the event of a change of orientation of the outer container.

There remains a need for organ transportation devices which will adequately maintain the organ in contact with both essential solutions, the preservation solution and the oxygen-dissolving solution.

SUMMARY OF THE INVENTION

An organ transportation device according to the invention comprises a fluid-tight organ container; structure within the organ container for engaging and securing an organ within the organ container and permitting the organ to contact fluid stored in the organ container; a base assembly; and means for rotating the organ securing structure and the organ relative to the base assembly.

The structure for securing the organ within the organ container can comprise a cage within the organ container, the cage defining an open interior having an interior volume. The cage can be adjustable to change the interior volume. The cage can comprise a plurality of elongated cage members. Means can be provided for rotating the elongated cage members. The means for rotating can comprise an end plate having slots for receiving ends of the elongated cage members. Rotation of the end plate causes movement of the ends through the slots and rotation of the cage members. A motor for rotating the organ container can be provided. The motor can be connected to the base assembly. A battery for powering the motor can be connected to the base assembly.

An organ transportation device comprises an organ container; means for rotating the organ container; and a cage within the organ container, the cage defining an open interior having an interior volume. The cage is adjustable to change the interior volume. The cage comprises a plurality of elongated cage members, and the cage members comprise a radial dimension in one axis greater than the radial dimension in another axis. Rotation about the elongated axis will move the greater radial dimension portion of the elongated cage members into or out of the interior volume.

The means for rotating the organ container can comprise a motor. The means for rotating the elongated cage members can comprise an end plate having slots for receiving ends of the elongated cage members. Rotation of the end plate causes movement of the ends through the slots and rotation of the cage members. The elongated cage members can be arranged about the circumference of an imaginary cylinder, so as to provide an open interior space for receiving and securing the organ.

A method for transporting an organ comprises the steps of: placing the organ in a fluid tight organ container; securing the organ within the organ container; sealing the organ container with the organ and a preservation solution there within; connecting the organ container to a portable base assembly having structure for rotating the organ relative to the base assembly; and, rotating the organ relative to the base assembly while transporting the organ container and base assembly.

BRIEF DESCRIPTION OF THE DRAWINGS

There are shown in the drawings embodiments which are presently preferred, it being understood, however, that the invention can be embodied in other forms without departing from the spirit or essential attributes thereof, wherein.

DETAILED DESCRIPTION OF THE INVENTION

There is shown in FIGS. 1-17 an organ transportation device 20 with an organ container 24 and a base assembly 28. The base assembly includes a motor for rotating the organ container 24 relative to the base assembly 28 such that an organ contained within the organ container 24 is caused to thoroughly contact a preservation media, such as a two-solution organ preservation media with a preservation solution and an oxygen-dissolving solution. An engagement structure such as a cage assembly 32 or other suitable structure can be provided within the organ container 24 to engage and secure the organ within the organ container 24. The engagement structure should secure the organ while permitting contact with the preservation media. The cage assembly 32 provides sufficient contact of the organ with the preservation media in the organ container 24. The cage assembly 32 or other engagement structure can be adjustable so as to secure different sized organs.

Figure 1:
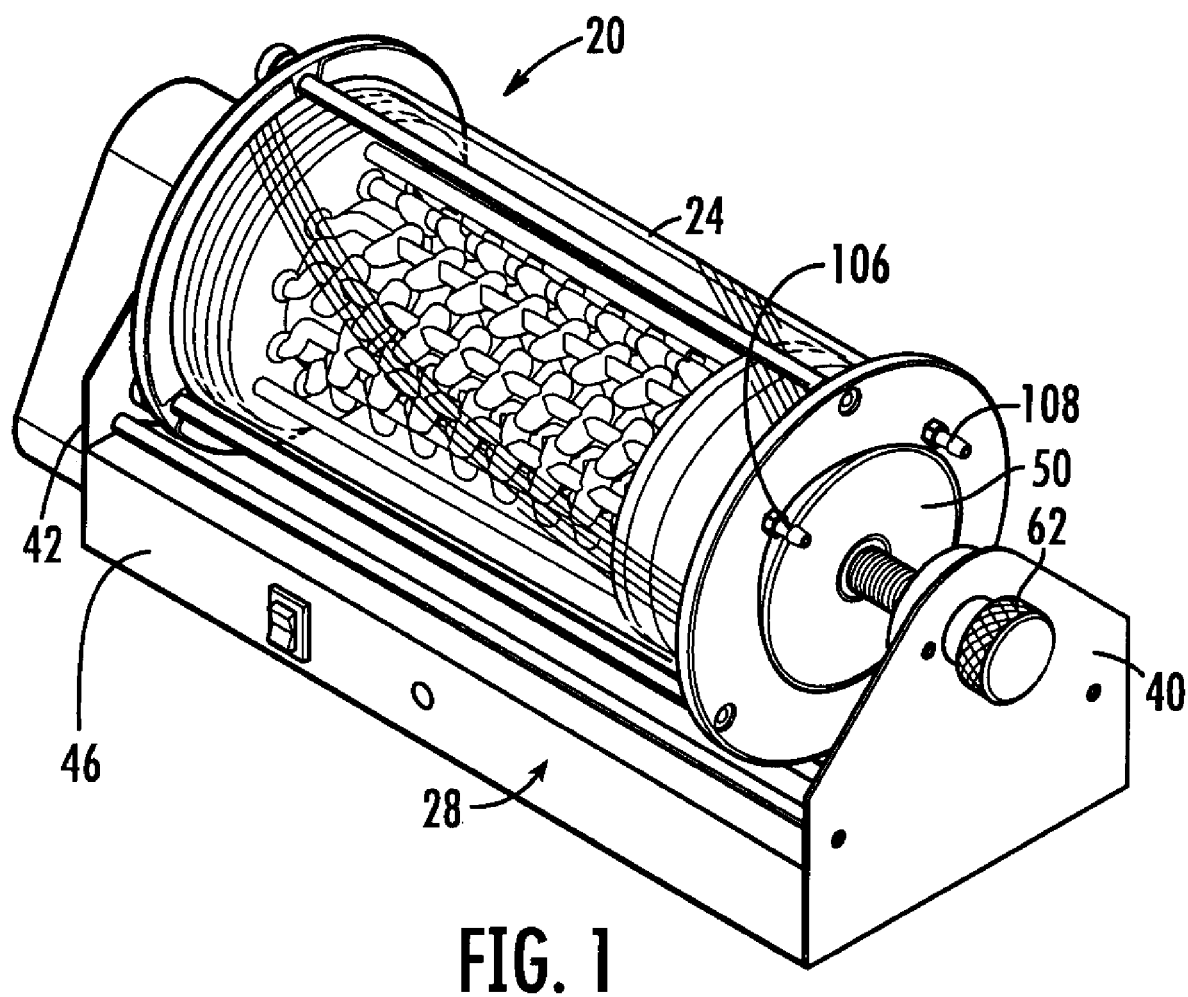
FIG. 1 is a perspective view of an organ transportation device according to the invention.
Figure 2:
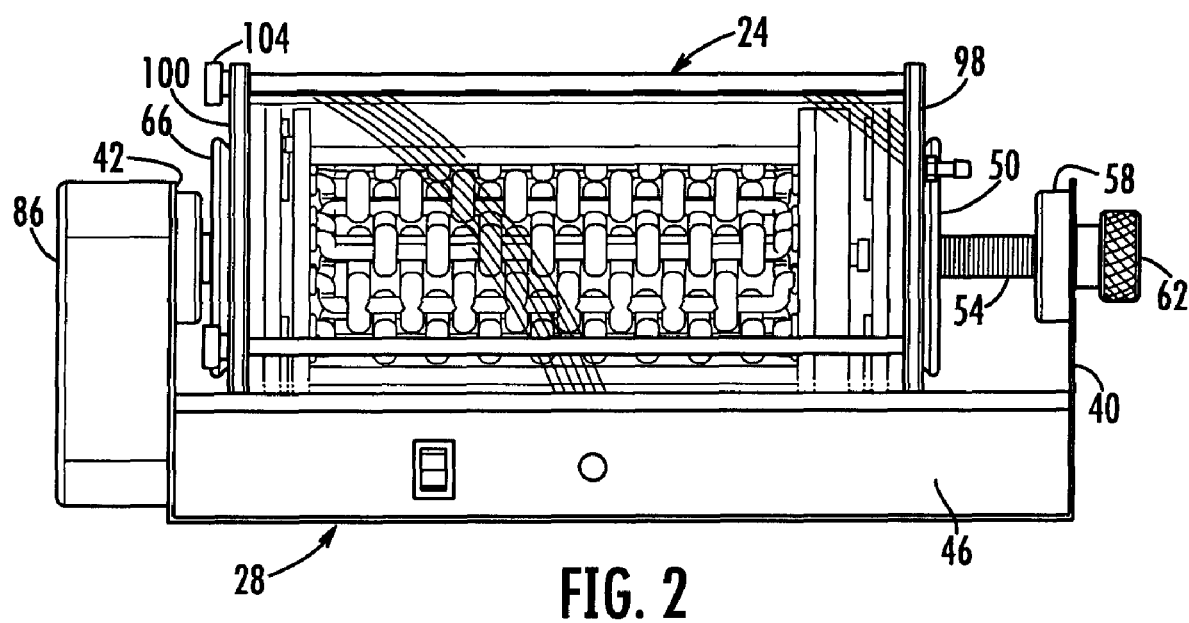
FIG. 2 is a front elevation.
Figure 3:
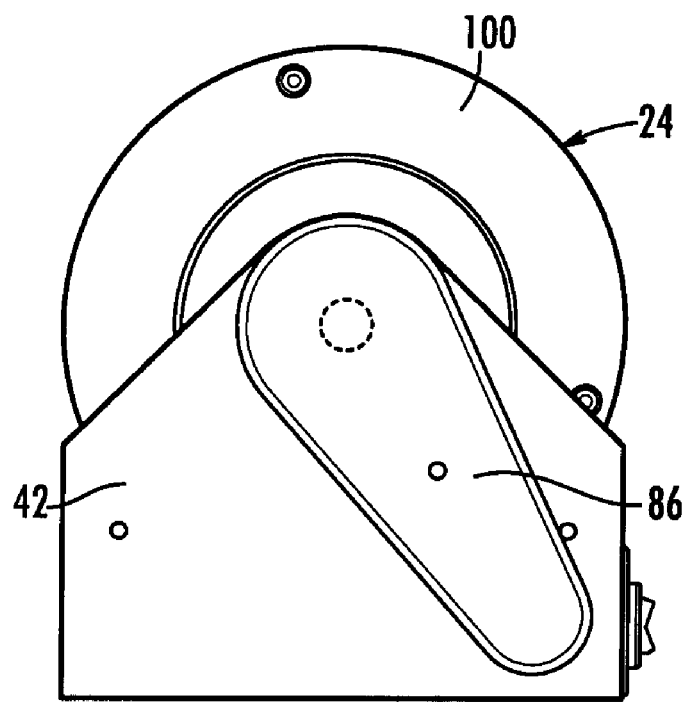
FIG. 3 is a left side elevation.
Figure 4:
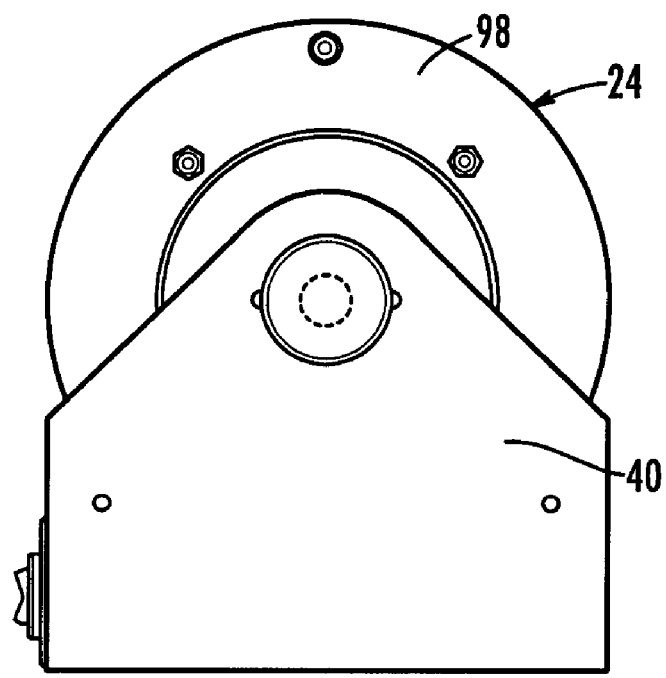
FIG. 4 is a right side elevation.
Figure 5:
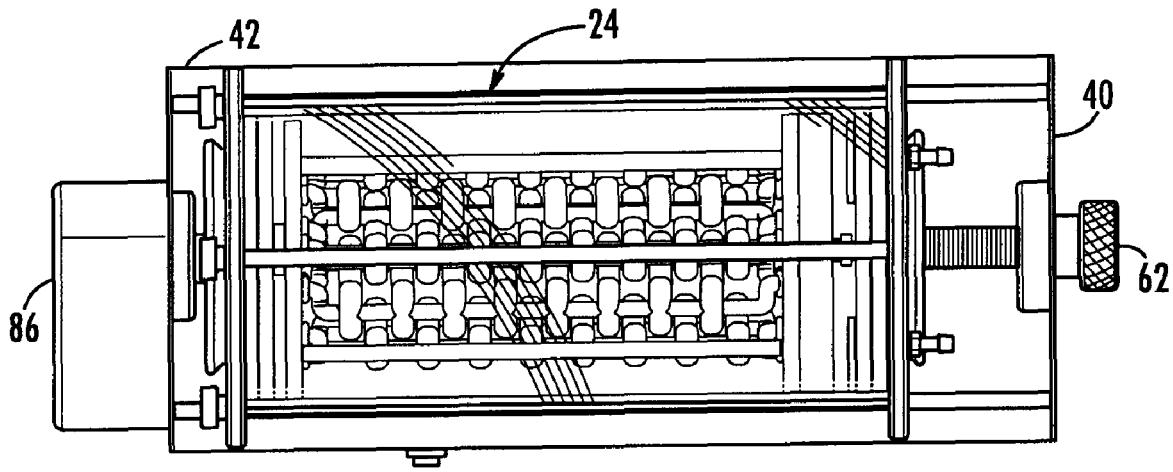
FIG. 5 is a top view.
Figure 6:
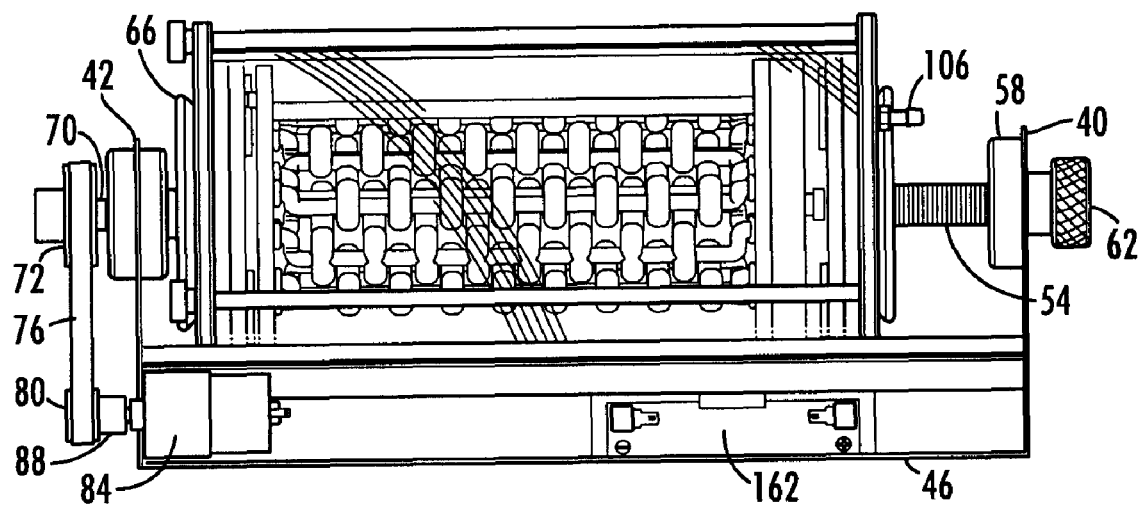
FIG. 6 is a front view with housing covers removed to reveal internal features.
Figure 7:
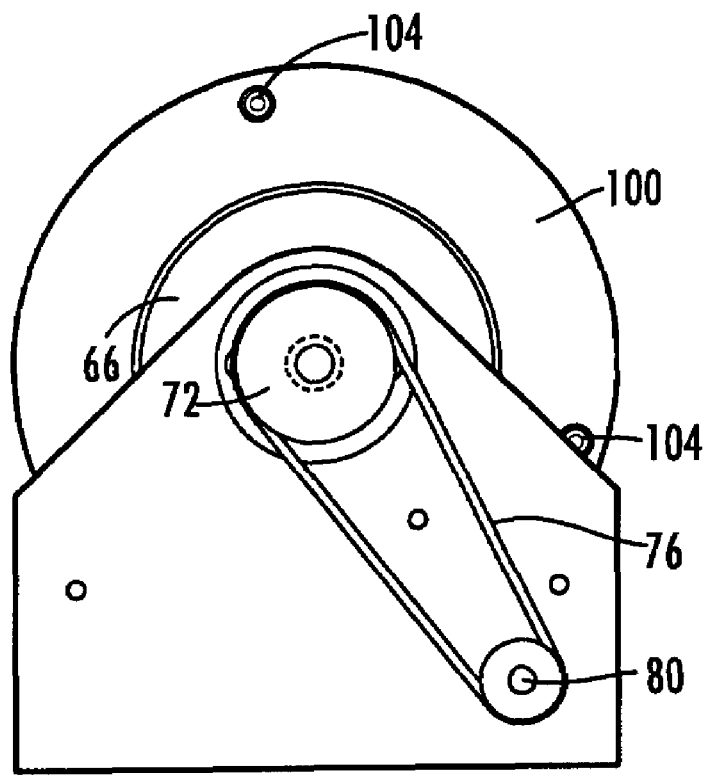
FIG. 7 is a left side elevation with a housing cover removed to reveal internal features.
Figure 8:
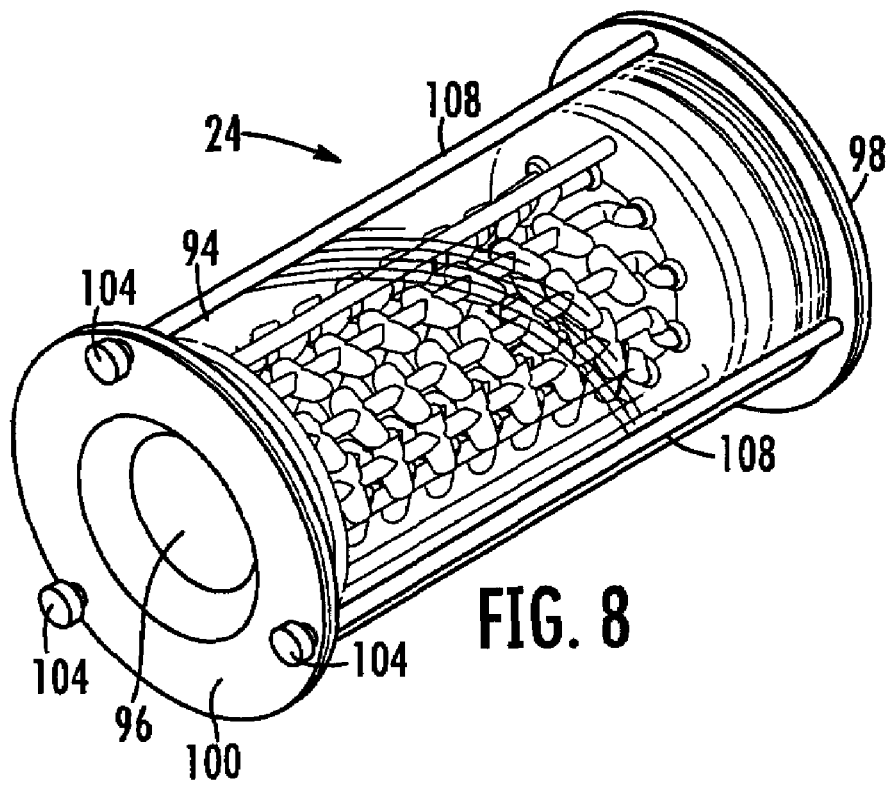
FIG. 8 is a perspective view of an organ container.
Figure 9:
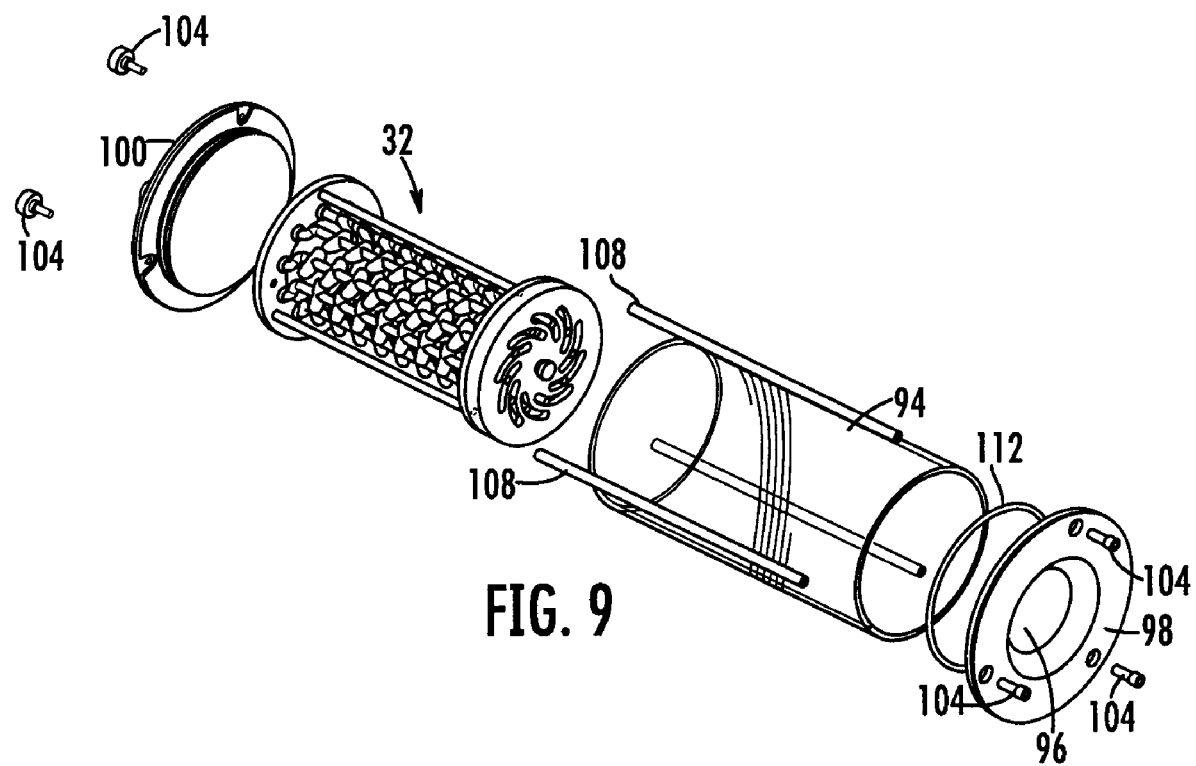
FIG. 9 is an exploded perspective view of an organ container.

The base assembly 28 can include structure for rotatably coupling to the organ container 24 so as to permit the rotation of the organ container 24 relative to the base assembly 28. It is alternatively possible to rotate the engagement structure within the organ container, and to fix the organ container relative to the base assembly 28. Any suitable structure for rotatably coupling the organ container 24 to the base assembly 28 can be utilized. In the embodiment shown, the base assembly 28 includes side frame plates 40, 42 which connect to a base housing 46. A clamp 50 can be rotatably connected to a threaded adjustment arm 54. The threaded adjustment arm 54 is engaged to a threaded aperture in a threaded member 58. An adjustment knob 62 is provided to rotate the adjustment arm 54 and advance or withdraw the clamp 50. Another clamp 66 is connected to a drive shaft 70 and a pulley 72 (FIG. 6). The pulley 72 is connected by a belt 76 to a pulley 80. The pulley 80 is driven by a shaft 88 that is rotated by a suitable motor 84. The motor 84 will thereby drive rotation of the clamp 66 and the organ container 24. A housing 86 can cover the pulley 72, pulley 80 and belt 76. Other drive structure for rotating the organ container 24 is possible, such as mounting a motor to the plate 42 or otherwise to a base assembly and rotating the organ container 24, or by providing the motor separate from the base assembly.

The organ container 24 can have different sizes, shapes, and constructions so long as it is fluid-tight and capable of retaining the organ and the preservation media. The organ container 24 shown in the drawings has a housing 94 with an open interior. The housing 94 can be tubular. End caps 98, 100 seal the open ends of the housing 94. Alternatively, the housing 94 can have one closed end and an open end, and a single end cap can seal the open end. Screws 104 or other suitable fastening structure can be provided to secure the end caps 98, 100 to support rods 108 to tighten the end caps 98, 100 against the housing 94. Alternatively, threaded apertures or other securing structure can be directly associated with the housing 94 to permit the end caps 98, 100 to be secured directly to the housing 94. O-ring seals 112 or other suitable structure can be used to provide a fluid-tight seal the connection between the end caps 98, 100 and the housing 94. Gas or liquid injection ports 106, 107 can be provided in one or both of the end caps 98, 100 to permit the introduction of liquids or gases such as oxygen into the organ container 24. The organ container 24 can be loaded with the preservation solution by injection through the ports 106, 107 or by pouring the solution into the container while in an upright position.

Figure 10:
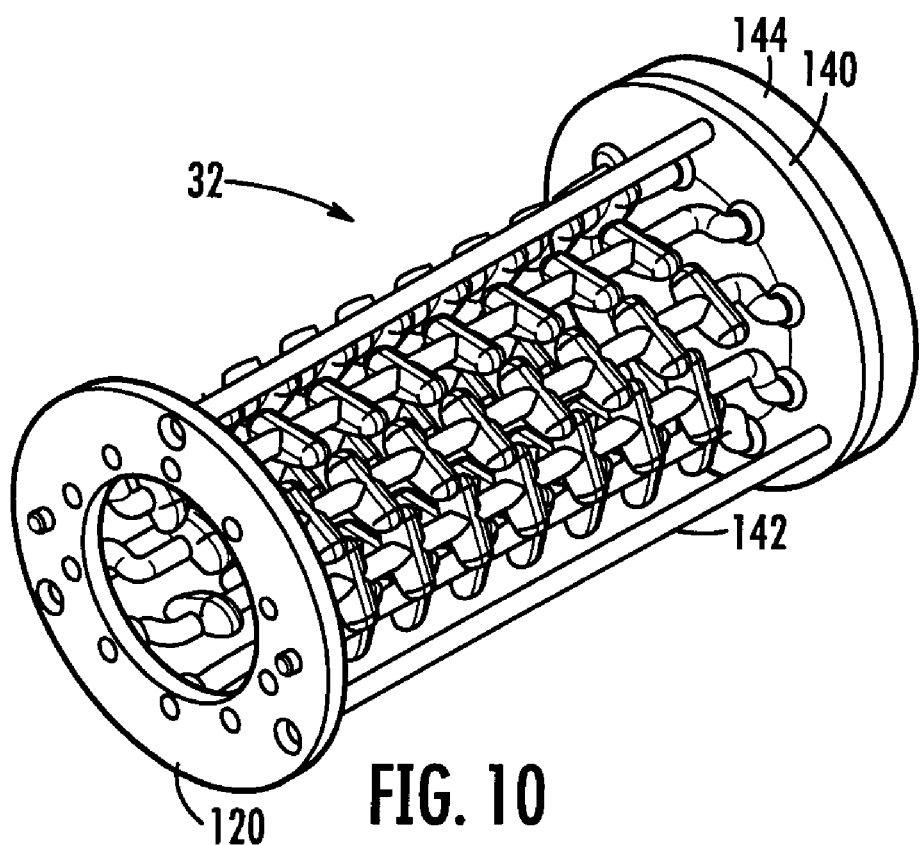
FIG. 10 is a left side perspective view of a cage assembly.
Figure 11:
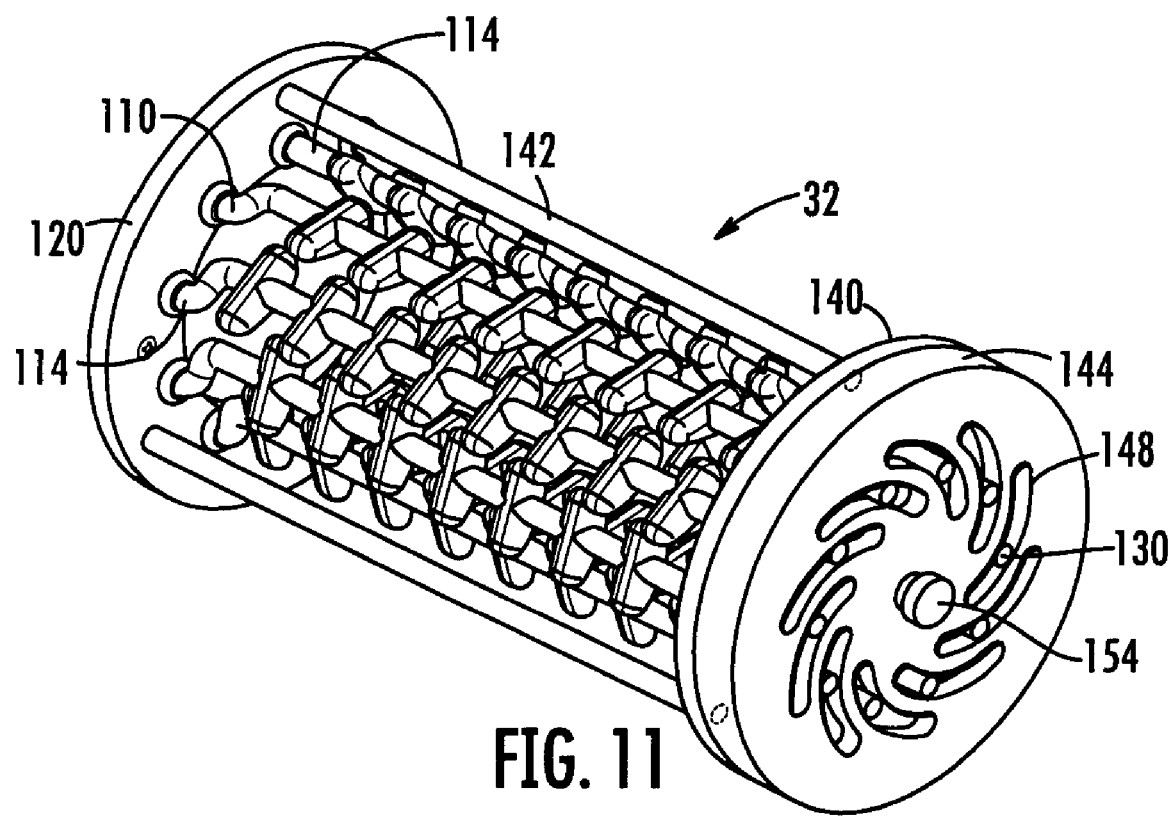
FIG. 11 is a right side perspective view of a cage assembly.
Figure 12A:
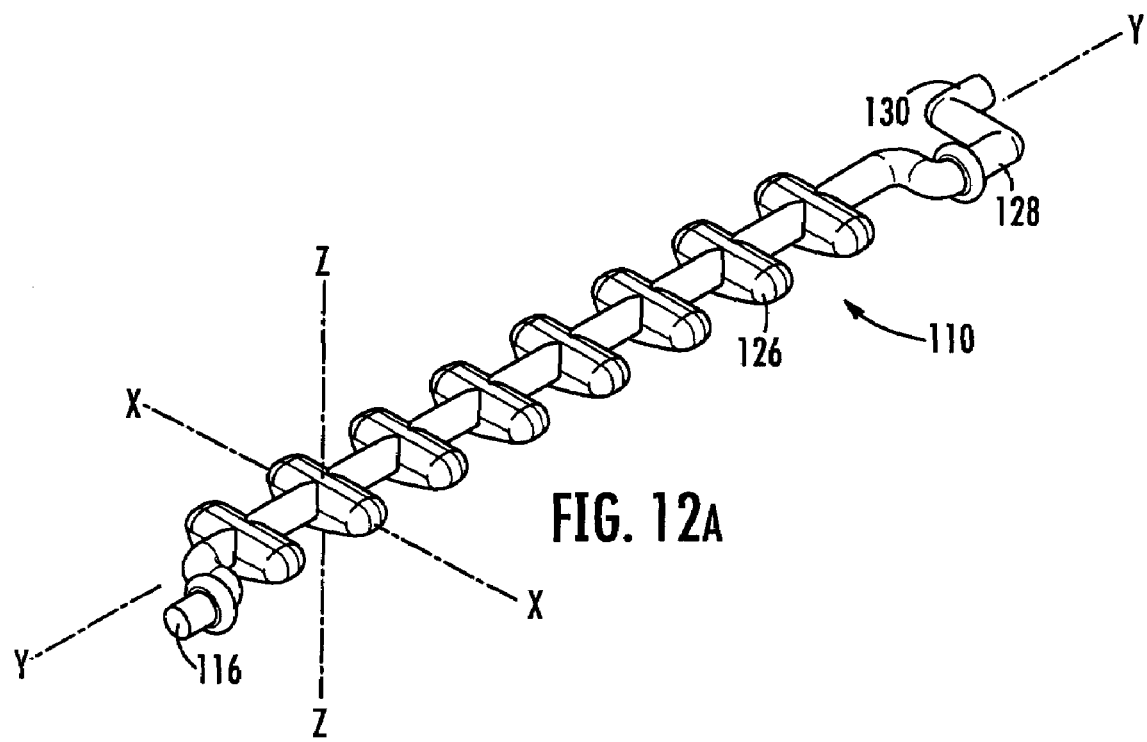
FIG. 12(a)-(b) are perspective views of elongated cage members.
Figure 12B:
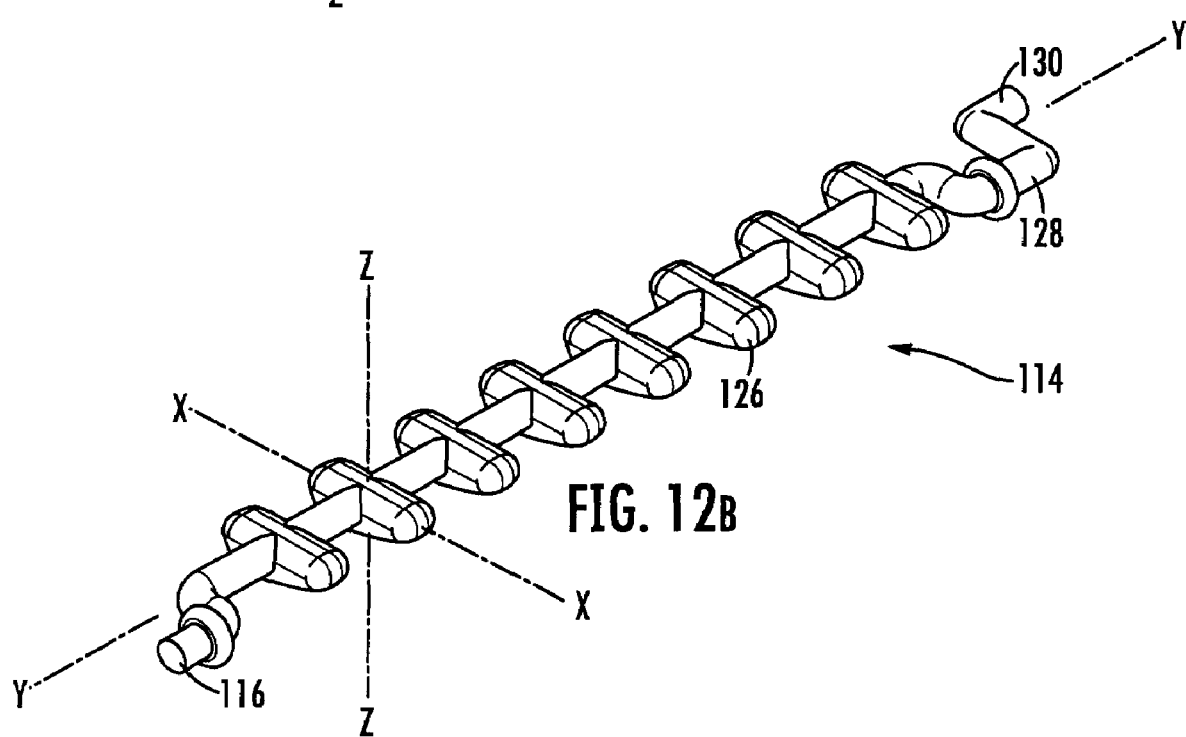
Figure 13:
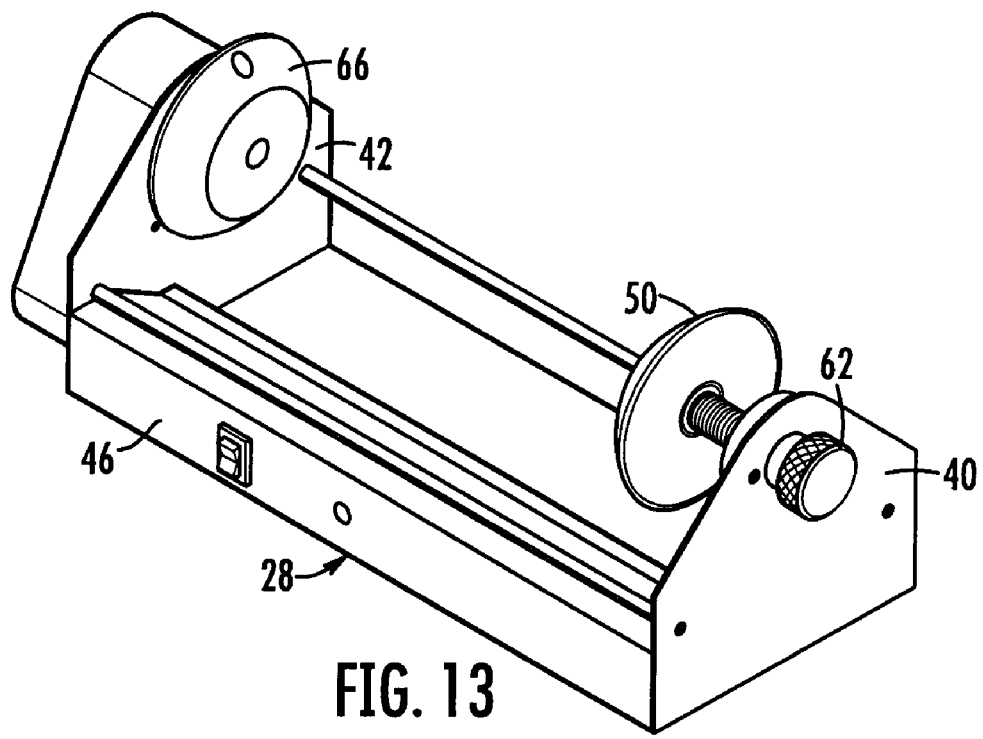
FIG. 13 is a right perspective view of a base assembly.
Figure 14:
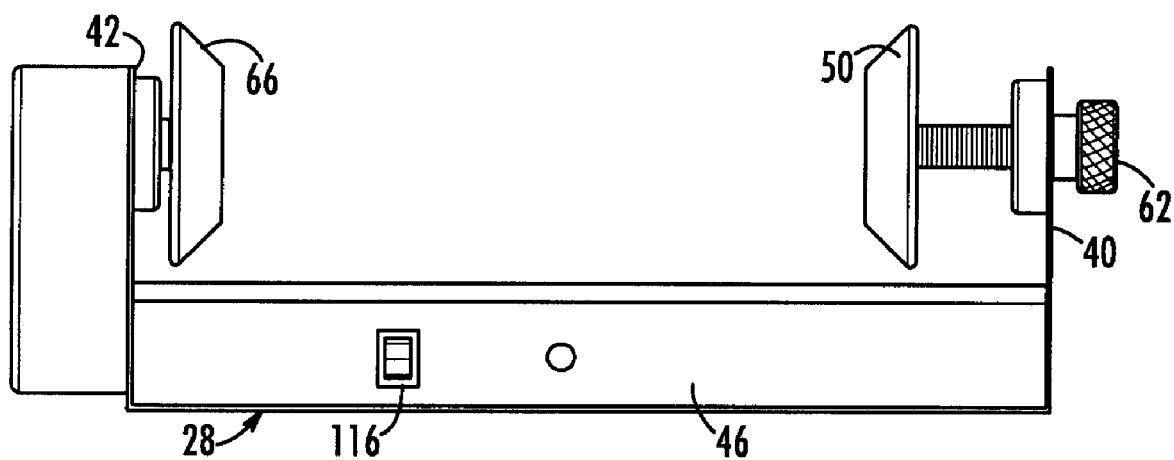
FIG. 14 is a front elevation of a base assembly.

The cage assembly 32 is shown in FIGS. 10-12. A plurality of elongated cage members 110, 114 are provided. Ends 116 of the cage members 110, 114 can be rotatably engaged to a first end support 120 so as to rotate about a long axis Y (FIG. 12). The cage members can be provided in a substantially cylindrical orientation, with cage members 110 alternating with cage members 114. The cage members have protrusions such that the radial dimension in one axis X is greater than the radial dimension in another axis Z. The protrusions can be in the shape of fingers 126. The fingers 126 of the cage members 110 can be spaced apart at distances that are offset from the positions of the fingers 126 on the cage members 114, such that when rotated in proximity to one another the fingers of adjacent cage members mesh rather than contact each other.

Figure 15A:
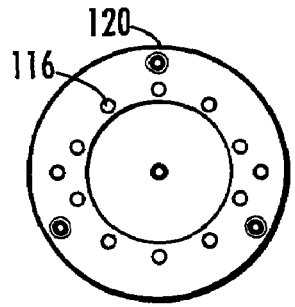
FIG. 15(*a*)-(*c*) are respectively left side, front, and right side elevations of a cage assembly in a first mode of operation.
Figure 15B:
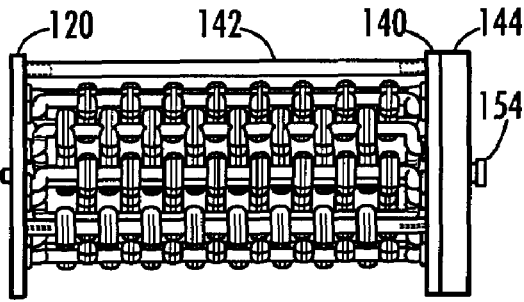
Figure 15C:
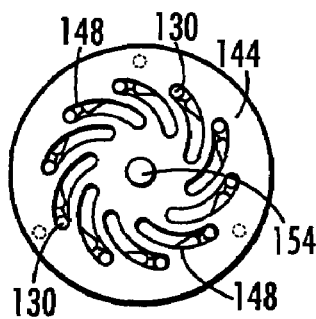
Figure 16A:
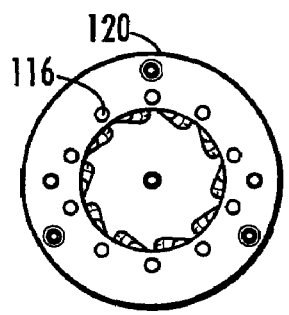
FIG. 16(*a*)-(*c*) are respectively left side, front, and right side elevations of a cage assembly in a second mode of operation.
Figure 16B:
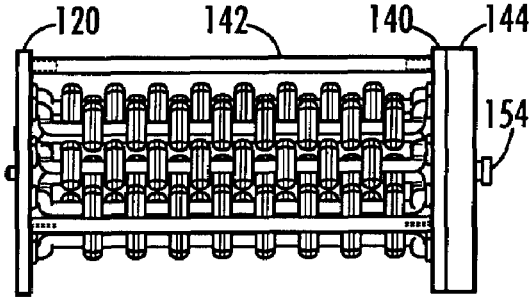
Figure 16C:
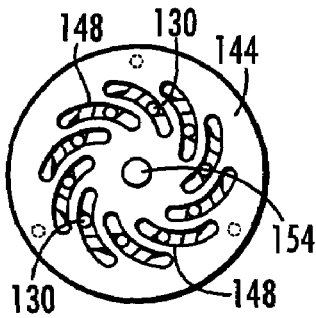
Figure 17A:
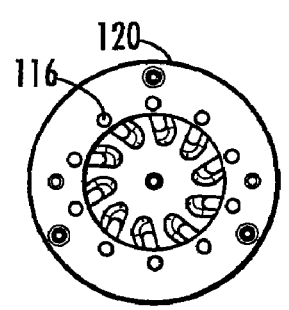
FIG. 17(*a*)-(*c*) are respectively left side, front, and right side elevations of a cage assembly in a third mode of operation.
Figure 17B:
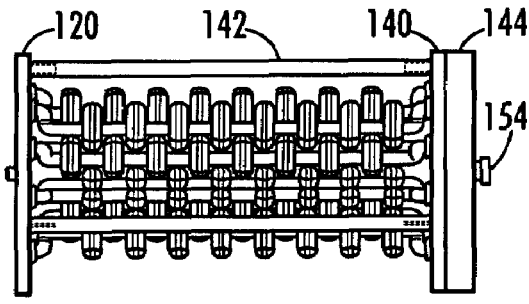
Figure 17C:
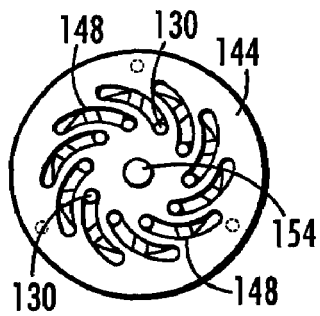

Rotation of the cage members can be accomplished in one aspect by rotatably engaging second ends 128 of the cage members 110, 114 in a second end support 140. The second end support 140 can be joined to the first end support 120 by suitable structure such as rods 142. A turning wheel 144 having slots 148 is rotatably engaged to the second end support 140. Offset portions 130 from the second ends 128 of the cage members 110, 114 are positioned in the slots 148 (FIG. 15). An adjustment screw 154 is provided to secure the turning wheel 144 against rotation. The adjustment screw 154 is loosened to permit rotation of the turning wheel 144, and then tightened to secure the turning wheel 144 in the desired position. Rotation of the turning wheel 144 to the intermediate position shown in FIG. 16 will move the slots 148 relative to the offset portions 130 (FIG. 16*c*), which will cause the cage members 110, 114 to rotate (FIG. 16*a-b*). The fingers 126 will rotate partially into the interior space of the organ container 24, effectively closing the cage assembly around the organ (not shown). Further rotation of the turning wheel 144 to the position shown in FIG. 17*c* will rotate the fingers 126 further into the interior of the organ container 24, closing the interior volume still further to engage a smaller organ (FIG. 17*a-b*). In this manner, the organ will be firmly but gently engaged within the cage assembly 32, and rotation of the organ container 24 will rotate the organ so as to thoroughly contact the organ with the preservation media, and particularly both layers when the media is a two layer media.

Other structure for engaging the organ within the organ container 24 is possible. It is preferable that such structure be adjustable such that different sizes of organs may be retained securely within the organ container 24. Securing the organ within the organ container will help to insure that the organ fully contacts the preservation media as the organ container 24 rotates, as otherwise the organ might float on the surface of the solution or at the interface of two solutions, and not adequately contact both solutions. The engagement structure should permit the preservation media to thoroughly contact the organ, and as such the contact area between the engagement structure and the organ should be as small as practical. Each of the fingers 126 touch the organ at only one point, and thereby leave much of the organ surface area open to contact by the solution. The organ can be stretched out along the long axis of the organ container 24, such that almost all surfaces of the organ will thoroughly contact the solution. Prior art shipping containers pack the organ tightly, preventing contact of some of the organ tissue with preservation solution, and preventing the organ from moving, such that portions of the organ will not contact both solutions of a two solution system. Other cage constructions are possible, for example, a flexible perforated sheet that can be rolled or wound about the organ to secure it.

The organ container 24 can be separated from the base assembly 28 by manipulation of the adjustment knob 62 to retract the clamp 50. The clamps 50, 66 can be shaped as partial cones which can be received in corresponding depressions 96 in the end caps 98, 100. Other mating structure is possible. Retraction of the clamp 50 thereby permits ready removal of the organ container 24 from the base assembly 28. The base assembly 28 as shown in FIGS. 13-14 can be used again, and the organ container 24 can be sterilized and reused or discarded and a new organ container can be used with the base assembly 28. A rechargeable battery can be provided (FIG. 6) to permit the base assembly to be reused. A switch 117 can be provided for operation of the motor 84.

The organ container 24 can be rotated at any desired speed. The motor or drive can be made adjustable such that the speed of rotation is adjustable. In one aspect the device will rotate at between about 1-5 revolutions per minute to constantly rotate the organ in and out of the preservation solution, although other speeds are possible. The rotation speed in another aspect can be adjusted by changing the pulley ratio. The device should preferably be capable of operation without external power for at least 24 hours. A fully charged sealed lead acid battery 162 can be provided for this purpose, such that electrical connections are not necessary during transportation.

The device can be constructed from disposable or non-disposable elements. The cage assembly 32 can be made from any suitable material. In one aspect, the material is polypropylene. The organ container 24 can have a housing 94 that is made from a clear plastic such as polycarbonate. The complete cage/tube assembly can be made from disposable components. The base assembly 28 is not in contact with the organ or preservation solution and can be reused without sterilization. The organ transportation device 20 can be placed inside an insulated shipping container where cold temperatures can be maintained and monitored for at least 24 hours. The insulated shipping container can be of any suitable construction, such as foamed polystyrene and other foamed polymers, double walled containers, and containers made from other insulating materials. The organ transportation device 20 can be constructed so as to be lightweight and portable having a weight less than about 50 pounds and a largest dimension less than about 3 feet.

This invention can be embodied in other forms without departing from the spirit or essential attributes thereof and, accordingly, reference should be had to the following claims rather than the foregoing specification as indicating the scope of the invention.

We claim:

1. An organ transportation device, comprising:
   a fluid-tight organ container;
   a structure within the organ container comprising a plurality of elongated cage members for engaging an organ within the organ container and permitting the organ to contact fluid stored in the organ container;
   a base assembly;
   means for rotating the organ engaging structure and the organ relative to the base assembly;
   and,
   means for rotating said elongated cage members, wherein said means for rotating said elongated cage members comprises an end plate having slots for receiving ends of said elongated cage members, rotation of said end plate causing movement of said ends through said slots and rotation of said cage members.

2. An organ transportation device, comprising:
   an organ container;
   means for rotating the organ container; and
   a cage within the organ container, said cage defining an open interior having an interior volume, said cage being adjustable to change said interior volume,
   wherein said cage comprises a plurality of elongated cage members, and
   wherein said cage members comprise a radial dimension about an elongated axis greater than the radial dimension about another axis, whereby rotation about the elongated axis will move said greater radial dimension into or out of said interior volume.

3. The organ transportation device of claim 1, wherein said elongated cage members form a cylinder.

4. The organ transportation device of claim 1, wherein said means for rotating comprises a motor.

5. The organ transportation device of claim 1, further comprising means for rotating said elongated cage members.

6. The organ transportation device of claim 1, wherein said means for rotating comprises an end plate having slots for receiving ends of said elongated cage members, rotation of said end plate causing movement of said ends through said slots and rotation of said cage members.

* * * * *